United States Patent [19]
McNichols

[11] 4,044,775
[45] Aug. 30, 1977

[54] IMPLANTABLE RECEIVER CIRCUIT

[75] Inventor: Larry A. McNichols, Coon Rapids, Minn.

[73] Assignee: Medtronic, Inc., Minneapolis, Minn.

[21] Appl. No.: 681,766

[22] Filed: Apr. 29, 1976

[51] Int. Cl.² ............................................. A61N 1/36
[52] U.S. Cl. ................................................ 128/421
[58] Field of Search ........ 128/419 C, 419 E, 419 PG, 128/420, 421, 422, 423

[56] References Cited

U.S. PATENT DOCUMENTS

| 3,204,637 | 9/1965 | Frank et al. | 128/423 W |
| 3,662,758 | 5/1972 | Glover | 128/419 E |
| 3,667,477 | 6/1972 | Susset et al. | 128/419 E |
| 3,893,463 | 7/1975 | Williams | 128/421 |

FOREIGN PATENT DOCUMENTS

| 985,797 | 3/1965 | United Kingdom | 128/419 PG |

*Primary Examiner*—William E. Kamm

*Attorney, Agent, or Firm*—Harry W. Barron; Joseph F. Briemayer

[57] ABSTRACT

In an implantable receiver circuit there is provided a tuned filter responsive to externally provided radio frequency energy bursts. The receiver also includes a pair of oppositely poled diodes for respectively providing positive and negative rectified versions of the energy bursts. The cathode of one diode is coupled through a low-pass filter circuit to an output capacitor and the anode of the other diode is coupled through a low-pass filter to the control electrode of a semiconductor switching device, the main electrodes of which are coupled between the output capacitor and the point of reference potential. With this connection the switching device is rendered conductive during the time no energy burst signals are applied to the tuned circuit thereby allowing the output capacitor to discharge during this time. During the time an energy burst is provided, the second rectifier circuit maintains the switching device non-conductive.

10 Claims, 2 Drawing Figures

IMPLANTABLE RECEIVER CIRCUIT

Background of the Invention

This invention relates to an implantable receiver for applying pulses through a lead to a selected body tissue, and more particularly to a circuit within said receiver for allowing a desired amplitude pulse to be provided to the tissue in response to a pulse being applied to that circuit.

In the prior art, as exemplified by U.S. Pat. No. 3,893,463, dated July 8, 1975 for DUAL CHANNEL STIMULATOR, in the name of Terrell M. Williams and assigned to the present assignee, there exists a transmitter and receiver system in which pulse bursts are applied from a transmitter external to the body through electrodes affixed to the skin and detected by an implanted receiver, which filters the pulse bursts and applies pulses to leads coupled between the receiver and selected body tissue. As used herein, the term "pulse burst" is defined as a series of radio frequency signal cycles occurring continuously for a desired time.

The implanted receiver circuit as shown in FIG. 3 of the Williams patent, is a dual channel receiver designed to detect and filter pulse burst signals having two different carrier frequencies. Each channel of the receiver circuit includes a rectifier for providing one polarity of the received alternating current signal to a filter, which consists of a parallel resistor-capacitor combination, having component values selected to eliminate the radio frequency carrier wave for that channel. After filtering, there remains a pulse signal having a duration equivalent to the duration of the radio frequency. Between the filter and the lead is an output capacitor through which the pulse signal is applied, thereby causing a signal to be provided to the lead and, hence, the tissue. The signal applied to the lead has a substantially instantaneous leading edge rise and an exponentially decaying trailing edge. The time constant of the exponentially decaying trailing edge is determined by the value of the output capacitor and the resistor value within the filter.

One problem with the above-described circuit is that as the frequency of the pulses applied to the output capacitor increases beyond a certain value, the output capacitor cannot completely discharge through the resistor of the filter. Thus, at the time a new pulse is provided, a substantial amount of DC bias remains in the capacitor, and in order to overcome this bias and provide a proper magnitude pulse to the tissue, it is necessary that the pulse provided to the capacitor be increased in magnitude. This, in turn, requires that the pulse provided external to the implanted receiver and detected thereby be increased in magnitude.

The external transmitting device is a battery-powered transmitter which is described in the above-mentioned patent. To increase the magnitude of the pulse generated by the external device, an extra drain on the battery powering the device is required. This, in turn, results in a shorter life for the battery and the additional expense and inconvenience to the patient in changing batteries.

SUMMARY OF THE INVENTION

In accordance with one aspect of this invention, there is provided a circuit included in a device implantable within a body for providing, at a given rate, pulses of a pulse signal to a lead connecting the device to bodily tissue. The device includes means responsive to a signal applied external to the body and radiated to the device for providing an internal signal manifesting the externally provided signal to the circuit, with the external signal being a series of alternating current pulse bursts which occur at a given rate. The circuit comprises first means responsive to the internal signal for providing a pulse during the occurrence of each of the pulse bursts, output energy storage means coupling the pulse to the lead, and second means switchably engaged for providing a low-resistance discharge path for the storage means during the time pulses of the pulse signal are not applied to the storage means.

BRIEF DESCRIPTION OF THE DRAWINGS

A preferred embodiment of the subject invention is hereafter described with reference being made to the following Figures, in which.

DESCRIPTION OF THE PREFERRED EMBODIMENT

Figure 1:
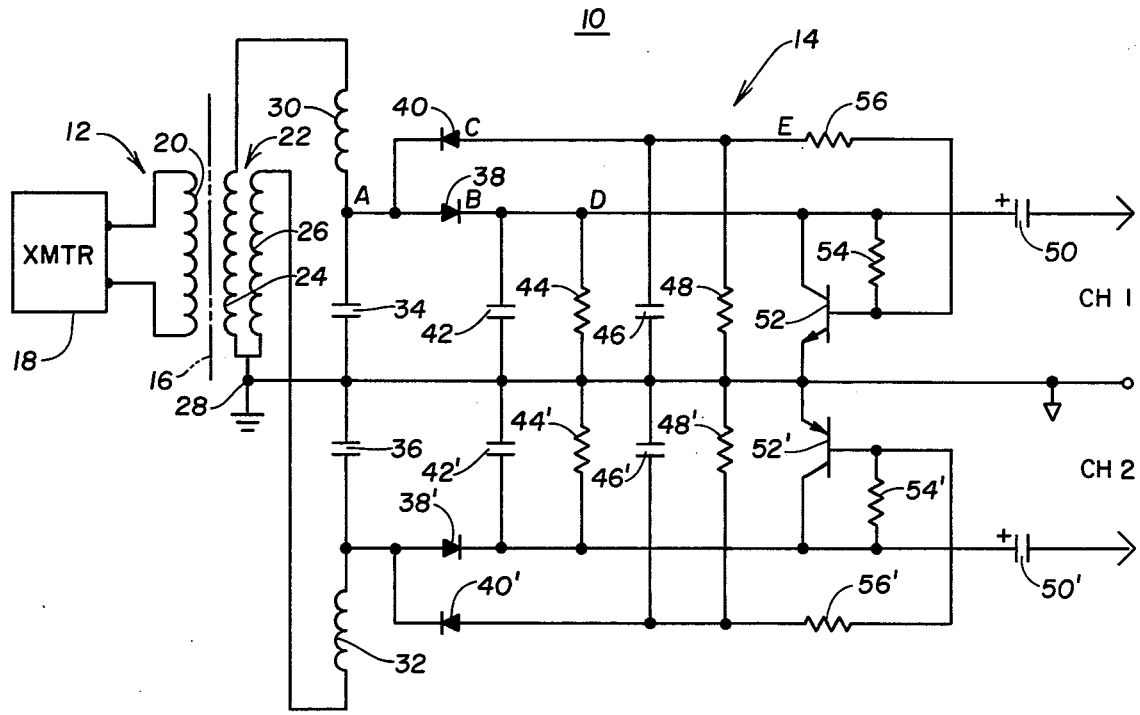
FIG. 1 is a circuit diagram of the receiver portion of an implanted dual channel stimulating device.

Referring now to FIG. 1, a dual channel stimulating device 10 is shown which includes a transmitter portion 12 and a receiver portion 14. Receiver portion 14 is implanted beneath the skin 16 of a human or other animal and receives radio frequency energy from transmitter portion 12 which includes a transmitter circuit 18 coupled to an antenna 20.

Receiver portion 14 is implanted beneath the skin such that receiver antenna 22 is in close proximity with the inner surface of the skin 16. In this manner, transmitter antenna 20 may be placed on the opposite side of skin 16 in alignment with receiver antenna 22, whereby the radio frequency signals transmitted from antenna 20 are received by antenna 22.

Receiver antenna 22 consists of two coils 24 and 26 which may be wound in parallel with respect to each other in a common winding but electrically isolated except at the common reference junction 28. Each of the coils 24 and 26 are coupled serially with respective second coils 30 and 32. A capacitor 34 is connected in parallel with the series coils 24 and 30 and a capacitor 36 is coupled in parallel with the serially coupled coils 26 and 32. The inductance value of coils 24 and 30 and the capacitance of capacitor 34 are selected such that a tuned circuit is formed which will respond only to the carrier frequency selected for channel one. Similarly, the conductance value of coils 26 and 32 and the capacitance of capacitor 36 are selected so that a second tuned circuit is formed which will respond only to the carrier frequency for channel two.

The connection between capacitors 34 and 36 is connected to junction 28 and this point serves as a point of reference potential, or ground, for dual channel receiver 14. The remaining portion of receiver 14 is divided into two equal channels, each designated as CH1 (channel one) and CH2 (channel two). For the sake of brevity, only channel one will be described in detail hereafter with primed like reference numbers being shown for like components in channel two.

The junction between capacitor 34 and coil 30 is connected to the anode of a rectifier such as diode 38 and also to the cathode of a rectifier, such as diode 40. The cathode of diode 38 is connected to one end of a parallel combination of capacitor 42 and resistor 44 which form a low-pass filter. The other ends of capacitor 42 and resistor 44 are connected to the point of reference potential. The anode of diode 40 is connected to one end of the parallel combination of capacitor 46 and resistor 48 which also form a low-pass filter and the other ends of capacitor 46 and resistor 48 are connected to the point of reference potential. In addition, the cathode of diode 38 is connected to one end of output capacitor 50, the other end of which is coupled through the lead (not shown) to the tissue to which the pulse is to be applied.

A transistor 52 is connected with its main electrodes between the junction of diode 38 and capacitor 50 and the point of reference potential. Specifically, the collector is connected to the junction of diode 38 and capacitor 50 and the emitter is connected to the point of reference potential. The base of transistor 52 is connected through a resistor 54 to the junction between capacitor 50 and diode 38 and also through a resistor 56 to the anode of diode 40.

In operation, a series of pulse burst signals are applied from transmitter 18 to electrode 20. These pulse bursts are controlled as to duration and magnitude of the carrier frequency and, in the dual channel stimulator shown in FIG. 1, may comprise two carrier frequencies each with independent width and magnitude controls.

Figure 2:
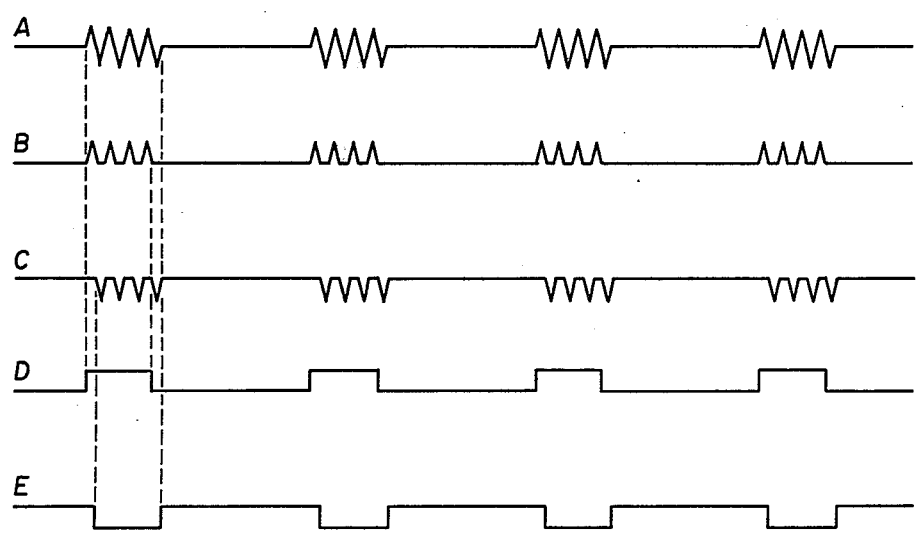
FIG. 2 is a series of waveforms useful in understanding the operation of FIG. 1.

Referring to FIG. 2, waveform A represents one of the two series of pulse bursts which are applied from transmitter 18. It should be noted that these bursts are of radio frequency, alternating current signals, and can be controlled by circuitry within transmitter 18 to last for variable periods of time and to be of variable amplitudes. The radiated pulse bursts from antenna 20 are inductively coupled to antenna 22 and applied through the appropriate tuned circuit, consisting of coils 24 and 30, and capacitor 34. From the tuned circuit, the alternating current waveform is rectified by diodes 38 and 40 such that waveform B is provided at the cathode of diode 38 and waveform C is provided at the anode of diode 40. After rectification, waveforms B and C are passed through low-pass filters consisting of capacitor 42 and resistor 44 for waveform B and capacitor 46 and resistor 48 for waveform C, and, thereafter appear respectively as waveforms D and E shown in FIG. 2. It should be noted that waveforms D and E are one-half of one radio frequency cycle out of phase with one another due to the operation of diodes 38 and 40. However, due to the high frequency of the radio frequency signals, this is negligible with respect to the pulse width.

At the time the pulse of waveform D is applied to output capacitor 50 and causes a jump on the lead side of capacitor 50, waveform E is at a negative value and maintains transistor 52 in a non-conductive state. After the leading edge of waveform D is applied to capacitor 50, the voltage across capacitor 50 builds up to the magnitude of the pulse of signal D.

After the conclusion of the positive pulse of signal D and the negative pulse of signal E, the voltage stored in capacitor 50 is applied through resistor 54 to render transistor 52 to the conductive state. With transistor 52 conductive, the voltage across capacitor 50 discharges through the low resistance path of conductive transistor 52. This discharge can readily be accomplished between the pulses of signals D and E.

If it were not for the provision of transistor 52, diode 40, resistors 54 and 56, and the filter consisting of capacitor 46 and resistor 48, and the various connections therebetween, capacitor 50 would be forced to discharge through resistor 44 which is a part of the low-pass filter. However, since resistor 44 must be in the order of a minimum of 5,000 ohms in order to be approximately ten times the size of the tissue resistance, which is in the order of 500 ohms, to avoid loading the circuit, the time constant between capacitor 50 and resistor 44 is large, and, thus, capacitor 50 cannot substantially discharge for rates above a certain level. However, with conductive transistor 52, the time constant comes very small and capacitor 50 can substantially discharge during the time between the pulses.

What is claimed is:

1. A circuit included in a device implantable within a body for providing at a given rate pulses of a pulse signal to a lead connecting said device to bodily tissue, said device including means responsive to a signal applied external to said body and radiated to said device for providing an internal signal manifesting said externally applied signal to said circuit, said external signal being a series of alternating current pulse bursts which occur at given rate, said circuit comprising:
   first means responsive to said internal signal for providing a pulse during the occurrence of each pulse burst;
   output energy storage means coupling said pulse signal to said lead; and
   second means switchably engaged for providing a low resistance discharge path for said storage means during the time pulses of said pulse signal are not applied to said storage means.

2. The invention according to claim 1 wherein said first means includes rectifier means and filter means, said rectifier means being responsive to said internal signal and providing an energy burst of one polarity to said filter means which in response thereto provides said pulse signal.

3. The invention according to claim 2 wherein said second means includes second rectifier means, second filter means, and signal controlled switch means, said second rectifier means being poled opposite to said first rectifier means, said second filter means being coupled between said second rectifier means and said switch means to provide a signal to open said switch means in response to the occurrence of each pulse signal and to close said switch means in response to the end of each pulse signal, said switch means, when closed, providing said discharge path.

4. The invention according to claim 3 wherein said energy storage means is a capacitor.

5. The invention according to claim 4 wherein said switch means is a transistor controlled to be non-conductive to open said switch means and conductive to close said switch means.

6. The invention according to claim 1 wherein said energy storage means is a capacitor.

7. The invention according to claim 1 wherein said second means includes a transistor controlled to be non-conductive during the time pulses are applied thereto and conductive at other times, said pulses applied to said transistor occurring during substantially the same time as the pulses of said pulse signal.

8. A circuit for use in an implantable device which provides pulse signals to electrically stimulate bodily tissue, said device including receiver means for detecting electrical signals applied external to said body but proximate thereto and for providing said detected signals to said circuit, said signals being radio frequency alternating current energy bursts occuring at a determined rate and magnitude, said circuit comprising:

a pair of oppositely poled rectifiers each coupled to said receiver means;

a filter for each rectifier for filtering the radio frequency from the signals provided by that rectifier to provide a pair of opposite polarity pulse series signals;

an output capacitor electrically coupled between one of said filters and said bodily tissue; and a semiconductor switching device having a pair of main electrodes coupled between the junction of said one filter and said capacitor and a point of reference and having a control electrode coupled to the output of said other filter, said switching device being poled to discharge said capacitor during the interim between pulses applied thereto.

9. The invention according to claim 8 wherein said filters each includes a parallel coupled resistor and capacitor, said resistor having a substantially greater resistance than the resistance of said bodily tissue, whereby said output capacitor cannot completely discharge through said filter resistor at rates of pulse signal provision above certain rates.

10. The invention according to claim 9 wherein said semiconductor switching device is a transistor having one main electrode coupled to said junction, the other main electrode coupled to said point of reference and a control electrode coupled through a first resistor to said junction and through a second resistor to said output of said other filter.

* * * * *